(12) United States Patent
Marino

(10) Patent No.: US 6,500,128 B2
(45) Date of Patent: Dec. 31, 2002

(54) NERVE MOVEMENT AND STATUS DETECTION SYSTEM AND METHOD

(75) Inventor: James F. Marino, La Jolla, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 09/877,713

(22) Filed: Jun. 8, 2001

(65) Prior Publication Data
US 2002/0007129 A1 Jan. 17, 2002

Related U.S. Application Data
(60) Provisional application No. 60/210,874, filed on Jun. 8, 2000.

(51) Int. Cl.[7] .................................................. A61B 5/05
(52) U.S. Cl. ........................................ 600/554; 600/546
(58) Field of Search ............................... 128/897–898, 128/920; 600/372, 373, 546, 548, 554; 607/43, 46, 48, 49

(56) References Cited

U.S. PATENT DOCUMENTS

| 2,704,064 A | 3/1955 | Fizzell et al. |
| 3,364,929 A | 1/1968 | Ide et al. |
| 3,664,329 A | 5/1972 | Naylor |
| 3,682,162 A | 8/1972 | Colyer |
| 3,830,226 A | 8/1974 | Staub et al. |
| 3,957,036 A | 5/1976 | Normann |
| 4,099,519 A | 7/1978 | Warren |
| 4,207,897 A | 6/1980 | Lloyd et al. |
| 4,224,949 A | 9/1980 | Scott et al. |
| 4,235,242 A | 11/1980 | Howson et al. |
| 4,285,347 A | 8/1981 | Hess |
| 4,291,705 A | 9/1981 | Severinghaus et al. |
| 4,515,168 A | 5/1985 | Chester et al. |
| 4,519,403 A | 5/1985 | Dickhudt |
| 4,545,374 A | 10/1985 | Jacobson |
| 4,592,369 A | 6/1986 | Davis et al. |
| 4,595,018 A * | 6/1986 | Rantala ...................... 600/546 |
| 4,633,889 A | 1/1987 | Talalla et al. |
| 4,658,835 A | 4/1987 | Pohndorf |
| 4,744,371 A | 5/1988 | Harris |
| 4,759,377 A | 7/1988 | Dykstra |
| 4,807,642 A | 2/1989 | Brown |
| 4,892,105 A | 1/1990 | Prass |
| 4,926,865 A | 5/1990 | Oman |

(List continued on next page.)

FOREIGN PATENT DOCUMENTS

WO    Wo 00/66217    11/2000

OTHER PUBLICATIONS

Ford et al., 'Electrical Characteristics of Peripheral Nerve Stimulators Implications for Nerve Localization' Regional Anesthesia (1984) 9:73–77.

(List continued on next page.)

*Primary Examiner*—Kennedy Schaetzle
*Assistant Examiner*—Kristen Droesch
(74) *Attorney, Agent, or Firm*—Jonathan Stangler

(57) ABSTRACT

A method and system for detecting nerve status and relative movement between a nerve and a proximity electrode. The method determines relative movement between a nerve and a proximity electrode by applying multiple signals to a calibration electrode where the energy level of each signal induces a predetermined nerve response. The method also applies multiple signals to the proximity electrode where the energy level of each signal also induces a predetermined nerve response. Based on the variation of the energy level of signals required to induce predetermined nerve responses, the method may detect relative movement between a nerve and a proximity electrode and nerve status.

23 Claims, 4 Drawing Sheets

U.S. PATENT DOCUMENTS

| | | |
|---|---|---|
| 4,962,766 A | 10/1990 | Herzon |
| 4,964,411 A | 10/1990 | Johnson et al. |
| 5,007,902 A | 4/1991 | Witt |
| 5,058,602 A | 10/1991 | Brody |
| 5,081,990 A | 1/1992 | Deletis |
| 5,092,344 A | 3/1992 | Lee et al. |
| 5,127,403 A | 7/1992 | Brownlee |
| 5,161,533 A | 11/1992 | Prass et al. |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,313,956 A | 5/1994 | Knutsson et al. |
| 5,327,902 A * | 7/1994 | Lemmen ..................... 600/547 |
| 5,333,618 A * | 8/1994 | Lekhtman et al. .......... 600/547 |
| 5,375,067 A | 12/1994 | Berchin |
| 5,482,038 A | 1/1996 | Ruff |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,579,781 A | 12/1996 | Cooke |
| 5,593,429 A | 1/1997 | Ruff |
| 5,630,813 A | 5/1997 | Kieturakis |
| 5,671,752 A | 9/1997 | Sinderby et al. |
| 5,711,307 A | 1/1998 | Smits |
| 5,775,331 A | 7/1998 | Raymond et al. |
| 5,779,642 A | 7/1998 | Nightengale |
| 5,797,854 A | 8/1998 | Hedgecock |
| 5,830,151 A | 11/1998 | Hadzic et al. |
| 5,851,191 A | 12/1998 | Gozani |
| 5,853,373 A | 12/1998 | Griffith et al. |
| 5,885,219 A | 3/1999 | Nightengale |
| 5,888,196 A | 3/1999 | Bonutti |
| 5,928,158 A | 7/1999 | Aristides |
| 5,976,094 A | 11/1999 | Gozani |
| 6,004,262 A | 12/1999 | Putz et al. |
| 6,038,477 A | 3/2000 | Kayyali |
| 6,050,992 A | 4/2000 | Nicholas |
| 6,132,386 A | 10/2000 | Gozani et al. |
| 6,132,387 A | 10/2000 | Gozani et al. |
| 6,146,335 A | 11/2000 | Gozani |
| 6,161,047 A | 12/2000 | King et al. |
| 6,224,549 B1 | 5/2001 | Drongelen |
| 6,259,945 B1 | 7/2001 | Epstein et al. |
| 6,266,558 B1 | 7/2001 | Gozani et al. |

OTHER PUBLICATIONS

Greenblatt et al., Needle Nerve Simulator–Locator; Nerve Blocks with a New Instrument for Locating Nerves Anesthesia & Analgesia (1962) 41 (5):599–602.

Martin et al., "Initiation of Erection and Semen Release by Rectal Probe Electrostimulation (RPE)" *The Williams & Wilkins Co.* (1983) pp.637–642.

Pither et al., "The Use of Peripheral Nerve Stimulators for Regional Anesthesia; Review of Experimental Charactersitics, Technique, and Clinical Applications" Regional Anesthesia (19850 10:47–53.

Raj et al., "Infraclavicular Bracjial Plexus Block—A New Approach" Anesthesia and Analgesia (1973) 52(6);897–.

Raj et al., Use of the Nerve Stimulators for Regional Anesthesia Clinical Issues in Regional Anesthesia (198501(40; 1–6.

Raj et al., "Use of Nerve Stimulators for Peripheral Blocks" Regional Anesthesia Apr.–Jun. 1980 pp. 14–21.

Raymond et al., The Nerve Seeker: A system for automated nerve localization Regional Anesthesia (1992) 17(30;151–162.

Shafik, "Cavernous Nerve Stimulation Through an Extrapelvic Subpubic Approach: Role in Penile Erection" Eur. Urol.(1994)26;98–102.

\* cited by examiner

NERVE MOVEMENT AND STATUS DETECTION SYSTEM AND METHOD

BACKGROUND OF THE INVENTION

1. Field of the Invention

This invention relates to nerve monitoring systems, and more particularly to relative nerve movement and status detection methods and systems.

2. Description of Related Art

Systems and methods exist for monitoring a nerve. One such system determines when a stimulating needle is approaching a nerve. The system applies a current to the needle to evoke a muscular response. The muscular response is visually monitored (typically as a shake or "twitch"). When the user observes such a muscular response, the needle is considered to be near the nerve coupled to the responsive muscle. These systems require the user to observe the muscular response (to determine that the needle has approached the nerve). This may be difficult depending on the competing tasks of the user. In addition, when general anesthesia is used during a procedure, muscular response may be suppressed, limiting the ability of a user to detect the response.

Accordingly, a need exists for a better system and method that can determine the movement and status of nerves.

SUMMARY OF THE INVENTION

The present invention includes a method and system for determining the status of a nerve and relative movement between a nerve and a conductive device. The present includes a method for determining relative movement between a nerve and a second conductive element. The method includes applying a first electrical signal to a first conductive element. The first conductive element is located at a position where the distance between the first conductive element and the nerve is relatively constant. The first electrical signal has an energy level that induces a predetermined nerve response. The method also applies a second electrical signal to the second conductive element. The second electrical signal has an energy level that induces the predetermined nerve response. Then the method applies a third electrical signal to the second conductive element. The third electrical signal has an energy level that induces the predetermined nerve response. When the current level of the third electrical signal is not substantially equal to the current level of the second electrical signal, the method applies a fourth electrical signal to the first conductive element. The fourth electrical signal has an energy level that induces the predetermined nerve response. Then, the method determines that relative movement between the nerve and the second conductive element has occurred when the energy level of the first electrical signal is substantially equal to the current level of the fourth electrical signal.

The method may further include placing a first conductive element at a position where the distance between the first conductive element and the nerve is relatively constant. The first electrical signal may have a current level that induces the predetermined nerve response. Further, the nerve response may be determined from at least one EMG measured at a muscle physiologically coupled to the nerve. The method may also include determining that the nerve status has changed when the energy level of the first electrical signal is not substantially equal to the energy level of the fourth electrical signal.

BRIEF DESCRIPTION OF THE DRAWINGS

Like reference numbers and designations in the various drawings indicate like elements.

DESCRIPTION OF THE SPECIFIC EMBODIMENTS

Throughout this description, the preferred embodiment and examples shown should be considered as exemplars, rather than as limitations on the present invention.

Figure 1:
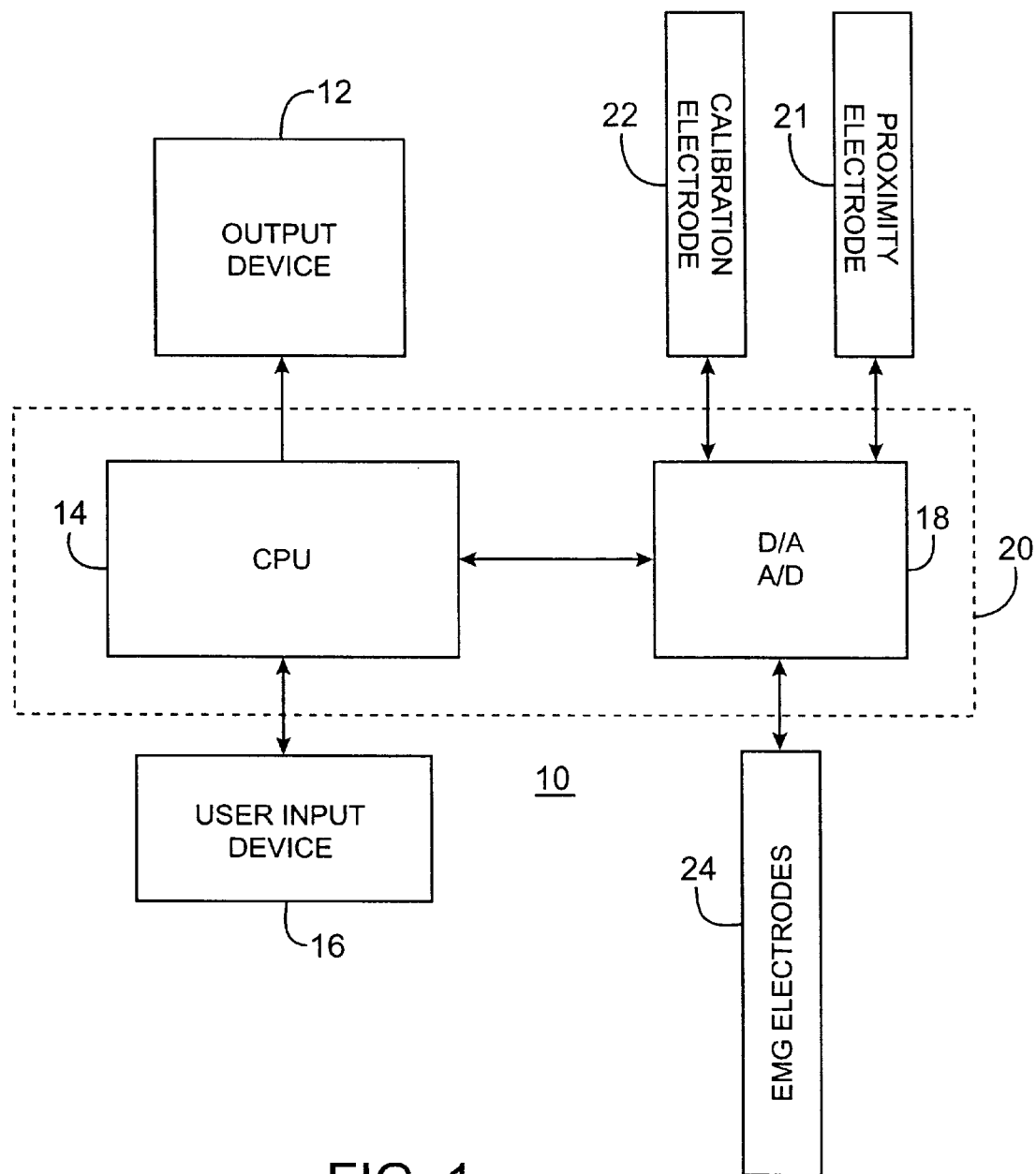
FIG. 1 is a block diagram of a nerve movement/status detection system in accordance with the present invention.

FIG. 1 is a diagram of an exemplary relative nerve movement and status system 10 in accordance with the present invention. The system 10 includes an output device 12, a user input device 16, a processor 20, a proximity electrode 21, a calibration electrode 22, and an electromyogram (EMG) electrode 24. The processor 20 includes a central processing unit ("CPU") 14 and a Digital to Analog converter ("D/A") and Analog to Digital Converter ("A/D") 18. The CPU 14 may be any microprocessor having sufficient processing power to control the operation of the D/A & A/D 18, and output device 12. The D/A & A/D 18 is any such device having a sufficient sampling rate and bit resolution to generate signals as described herein. The calibration electrode 22 is an electrode suitable for placement at a location where the distance to a nerve of a patient to be monitored is relatively constant. The EMG electrode 24 is an electrode(s) capable of detecting an EMG response where the electrode(s) may be inserted into a muscle physiologically coupled to the nerve to be monitored or placed on skin above the muscle. The proximity electrode 21 is an electrode that may be coupled to any medical device including a cannula, pedicle probe, needle, catheter, RF ablation device, medical laser, or other medical instrument. The proximity electrode 21 may include a single electrode (mono-polar), two electrodes (bipolar), or a plurality of electrodes (multi-polar) configuration.

The CPU 14 controls the operation of the D/A & A/D 18 and output device 12 based on user selection received via the user input device 16. The user input device 16 may be any input device including a keyboard, mouse, and touch sensitive screen. The output device 12 may be any user readable output device controllable by the CPU 14 such as computer monitor, printer, and other computer controlled display device. The system 10 generates electrical stimulus signals that are transmitted to the electrodes 21 and 22. The system interaction is described with reference to FIG. 2. The system 10 also receives signals from the EMG electrode 24. In general, the system 10 generates an electrical stimulus signal for the electrodes 21 and 22 via the D/A 18. In particular, the CPU 14 generates a digital representation of stimulus signals to be transmitted by the electrodes 21 and 22. The D/A converts the digital signals to analog stimulus signals that are transmitted by the electrodes 21 and 22. The stimulus signals are used to induce a nerve response in one or more nerves of interest located near or about the electrodes 21 and 22.

Figure 3A:
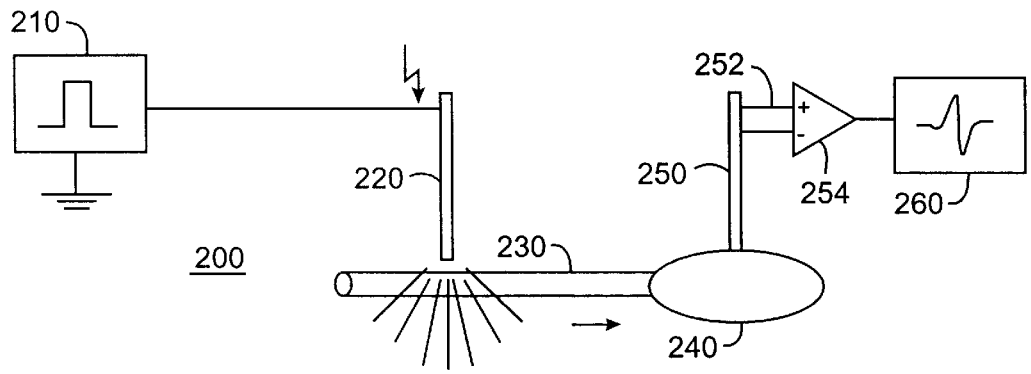
FIG. 3A is an illustrative diagram of a nerve stimulation and nerve response system according to the present invention.
Figure 3B:
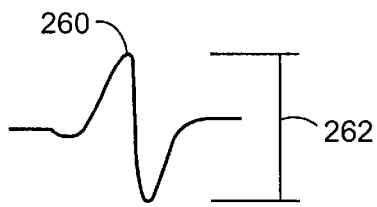
FIG. 3B is a simplified diagram of an EMG according to the present invention.
Figure 3C:
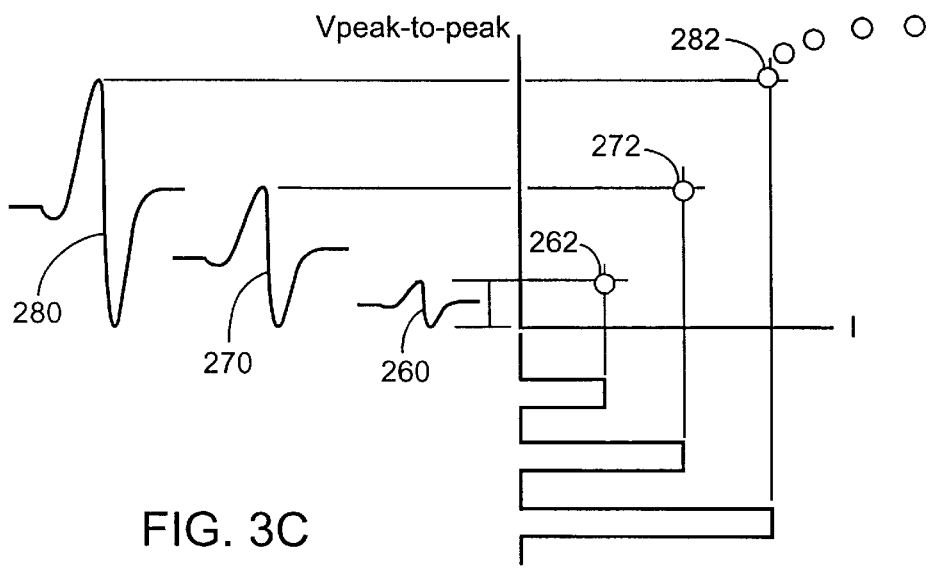
FIG. 3C is a diagram showing a mapping of the peak-to-peak voltage of EMG signal versus input signal current level according to the present invention.

An exemplary induce, nerve response is an EMG derived from a muscle physiologically coupled to the nerve(s) of interest. FIGS. 3A to 3C depict an exemplary method of determining a nerve response to a stimulus signal according to the present invention. FIG. 3A is an illustrative diagram of a nerve stimulation and nerve response system 200 according to the present invention. The system depicts a plot of a stimulus pulse 210, stimulus electrode 220, nerve 230, muscle 240 physiologically coupled to the nerve 230, EMG electrodes 250, differential pair 252, differential amplifier 254, and plot of EMG signal 260. In this exemplary system 200, a stimulus signal having a fixed current level and having the shape shown in the plot 210 is applied to the stimulus electrode 220. The stimulus electrode 220 may be a proximity or calibration electrode. The stimulus electrode 220 is located near or about a nerve 230 of interest. The stimulus electrode 220 radiates the stimulus signal to the nerve 230. The nerve 230 may generate a response (depolarize) when the energy level of the stimulus signal 210 is sufficient. When the nerve is depolarized, the nerve may innervate the muscle fibers 240. The EMG electrodes 250 conduct any electrical activity in the muscle fibers 240. The electrodes are coupled to the differential amplifier 254 by the differential pair of wires 252. The differential amplifier 254 may generate an EMG similar to the simplified EMG plot 260.

The present invention determines the induced nerve response (from a stimulus signal applied to a stimulus electrode), by measuring the maximum peak-to-peak voltage response of the EMG generated from a muscle physiologically coupled to the nerve. FIG. 3B is a simplified plot of an EMG according to the present invention where the peak-to-peak response (magnitude) 262 is shown. In one embodiment, the invention may increase the current level of the stimulus signal applied to the stimulus electrode 220 until the maximum peak-to-peak EMG voltage response reaches some predetermined minimum value. In another embodiment, the invention generates a mapping of the maximum EMG peak-to-peak voltage level versus the input signal current level. Such an exemplary mapping is shown in FIG. 3C. In this example, the maximum EMG peak-topeak voltage level 262, 272, and 282 for three EMG signals 260, 270, and 280 are mapped relative to the stimulus signal current level. A curve that best fits through these mappings is termed an S-curve or recruitment curve.

Figure 4A:
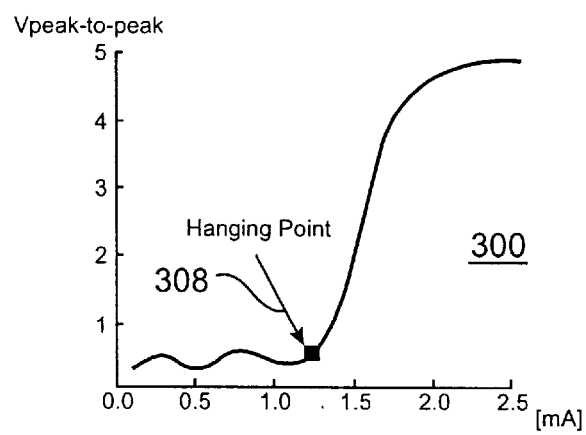
FIG. 4A is an exemplary graph of the peak-to-peak voltage level of EMG response versus input signal current level according to the present invention.
Figure 4B:
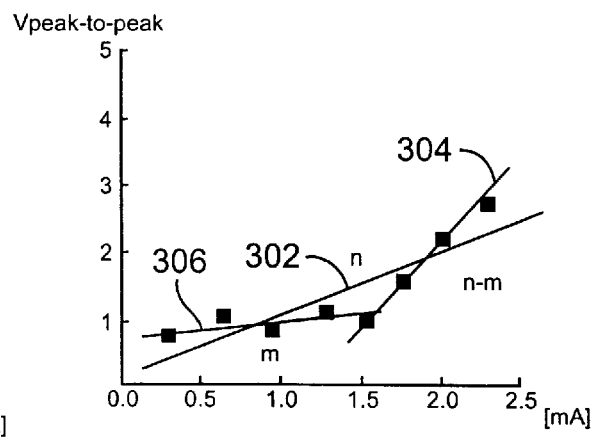
FIG. 4B is a diagram of an exemplary method of determining a hanging point of the curve shown in FIG. 4A according to the present invention.
Figure 4C:
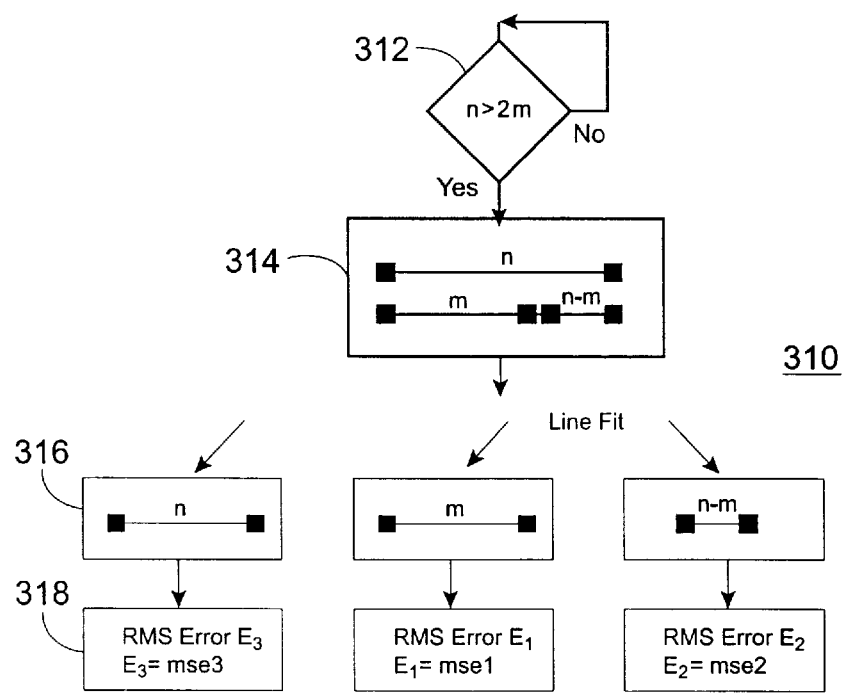
FIG. 4C is a flowchart of the exemplary method of determining the hanging point of the curve shown in FIG. 4A according to the present invention.

In one exemplary embodiment, the stimulus current level is increased until a particular point on the recruitment curve is located. Then the stimulus current associated with the predetermined point on the recruitment curve is selected as the current level required to induce the predetermined nerve response. FIG. 4A is an exemplary plot of such a recruitment curve with a predetermined point 308 selected where the point is termed the hanging point. Accordingly, the stimulus current level (about 12 mA in this example) that corresponds to the hanging point of the recruitment curve is designated as the current level that induces a predetermined nerve response according to one exemplary embodiment of the invention. FIGS. 4B and 4C illustrate one exemplary method of determining the location of a hanging point of a recruitment curve.

As noted, the recruitment curve is comprised of individual mapping points of EMG peak-to-peak voltage versus stimulus signal current level (such as shown in FIGS. 3C and 4B). The method locates the "hanging point" of the recruitment curve by accumulating a number of such mapping points and then attempting to fit three different lines segments through this minimum number of points. As shown in FIG. 4C, the first step 312 determines whether there are a sufficient number of mappings. In one exemplary embodiment the method waits until there are at least 2*m points (n>2 m) where m is the minimum number of points that may be used to generate one of the three lines segments. In one embodiment, m is at least 7, so n is at least 15 before the method is employed. Then the method (steps 314, 316) determines:

a) the line segment that best fits all n points, shown as line 302 in FIG. 4B;

b) the line segment that best fits the first m points, shown as line 306 in FIG. 4B; and c) the line segment that best fits the last n-m points, shown as line 304 in FIG. 4B.

The parameters of these three line segments are determined using linear regression in one embodiment. Then, the method determines how well each line segment fits the mappings. In one embodiment, the fit for each segment is determined by calculating the root mean square ("RMS") error for each line segment versus mappings (step 318). The calculated RMS error for lines 302, 306, and 304 are termed E3, E1, and E2. The method determines that the mth point (mapping) is the hanging point when $$C1*E1+C2*E2<E3.$$

In this equation C1 and C2 are calibration constants and each are less than one. This equation indicates that the two smaller line segments 304 and 306 better fit the mappings than the single line segment 302.

The method may also monitor the slope of the line segments 302, 304, 306. When the slopes of the line segments are similar, the method may determine that the first point (mapping) represents the hanging point of the recruitment curve. This situation may occur when the stimulus electrode is a sufficient distance from the nerve that the first measurable EMG response is the also the hanging point. In order to perform this exemplary method, the EMG electrode 24 receives EMG or evoked muscle action potential ("EMAP") signals generated by muscle fiber 240 electrically coupled to the EMG electrodes 24. In the present invention, the nerve is stimulated by an electrical signal transmitted by electrode 21 or 22. The A/D 18 converts the analog signal received by the EMG electrode 24 (after processing by the differential amplifier 254) into a digital signal that may be processed by the CPU 14.

Figure 2:
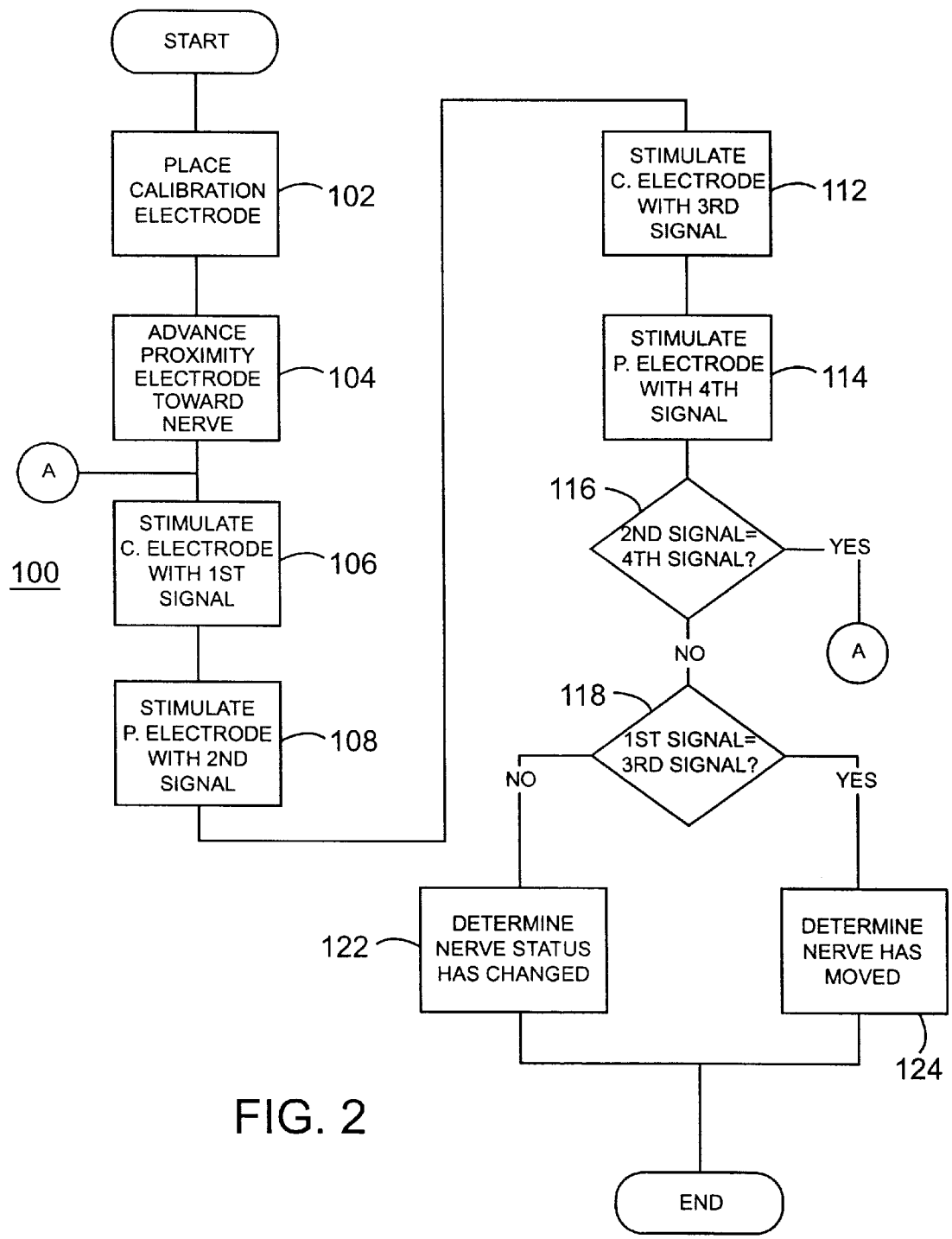
FIG. 2 is a flowchart of an exemplary method of determining nerve movement or status change in accordance with the present invention.

FIG. 2 depicts an exemplary method 100 of determining relative movement between a nerve and a proximity electrode where a calibration electrode is placed at a location that is a constant distance from the nerve during the execution of the method. The method 100 places a calibration electrode at a location that is a constant or fixed distance from the nerve (step 102). Ideally, the distance between the calibration electrode and nerve remains constant or fixed during the execution of the method. In one embodiment, the calibration electrode is placed in the epidural space above the dura of the spinal cord and between the spinous processes near the nerve of interest and midline to the spinal cord.

A proximity electrode may be placed at some desired location or a clinician may be manipulating a tool including the electrode (step 104). The calibration electrode is stimulated with a first signal whose current level is induces the predetermined nerve response (step 106). As shown with reference to FIGS. 4A, 4B, and 4C, the process of determining the first signal current level that induces the predetermined nerve response may include mapping the recruitment curve and finding the stimulus current level that corresponds to the hanging point of the recruitment curve. The proximity electrode is then stimulated with a second signal whose current level induces the predetermined nerve response (step 108).

Because this method may be executed during a procedure where the relative distance between the proximity electrode and nerve may change, the method repeats these steps and then determines whether any changes (nerve status or relative distance/movement) have occurred. Accordingly, the calibration electrode is then stimulated with a third signal whose current level induces the predetermined nerve response (step 112). The proximity electrode is stimulated with a fourth signal whose current level induces the predetermined nerve response (step 114). Then the electrodes stimulus current levels (that induced the predetermined nerve response) are compared to determine whether relative movement between the nerve and the proximity electrode has occurred, the nerve status has changed, or no detectable change has occurred. First (at step 116), the second signal current level is compared to the fourth signal current level. When the current levels of these signals are substantially the same, no change has likely occurred, i.e., no relative movement between the nerve and the proximity electrode has occurred and the nerve status has not changed. Note: step 112 may be bypassed when these levels are substantially equal.

When the second signal current level is not substantially equal to the fourth signal current level, then one of the nerve status and the relative distance between the nerve and the proximity electrode has changed. In order to determine which has changed, the method 100 (at step 118) compares the first signal current level to the third signal current level (for the calibration electrode). Given the relative distance between the calibration electrode and nerve is constant during the execution of the method, the current level required to induce the predetermined nerve response should remain constant unless the nerve health or status has changed. When these levels (first signal and third signal current levels) are equal the method determines that the relative distance between the nerve and the proximity electrode has changed (step 124). Otherwise, the method 100 determines that at least the nerve status has changed (step 122).

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution.

As can be envisioned by one of skill in the art, many different combinations of the above may be used and accordingly the present invention is not limited by the scope of the appended claims.

What is claimed is:

1. An apparatus for determining nerve status, the apparatus including:
   (a) means for applying a first electrical signal to a first conductive element where the first conductive element is located at a position where the distance between the first conductive element and the nerve is relatively constant and the first electrical signal has an energy level that induces a predetermined nerve response;
   (b) means for applying a second electrical signal to a second conductive element where the second electrical signal has an energy level that induces the predetermined nerve response;
   (c) means for applying a third electrical signal to the second conductive element where the third electrical signal has an energy level that induces the predetermined nerve response;
   (d) means for applying a fourth electrical signal to the first conductive element where the fourth electrical signal has an energy level that induces the predetermined nerve response when the energy level of the third electrical signal is not substantially equal to the energy level of the second electrical signal; and
   (e) means for determining the nerve status has changed when the energy level of the first electrical signal is not substantially equal to the energy level of the fourth electrical signal.

2. The apparatus of claim 1, wherein the first electrical signal has a current level that induces the predetermined nerve response.

3. The apparatus of claim 1, wherein the nerve response is determined from at least one EMG measured at a muscle physiologically coupled to the nerve.

4. An apparatus for determining relative movement between a nerve and a second conductive element, the apparatus including:
   (a) means for applying a first electrical signal to a first conductive element where the first conductive element is located at a position where the distance between the first conductive element and the nerve is relatively constant and the first electrical signal has an energy level that induces a predetermined nerve response;
   (b) means for applying a second electrical signal to the second conductive element where the second electrical signal has an energy level that induces the predetermined nerve response;
   (c) means for applying a third electrical signal to the second conductive element where the third electrical signal has an energy level that induces the predetermined nerve response;
   (d) means for applying a fourth electrical signal to the first conductive element where the fourth electrical signal has an energy level that induces the predetermined nerve response when the energy level of the third electrical signal is not substantially equal to the energy level of the second electrical signal; and (e) means for determining that relative movement between the nerve and the second conductive element has occurred when the energy level of the first electrical signal is substantially equal to the energy level of the fourth electrical signal.

5. The apparatus of claim 4, wherein the first electrical signal has a current level that induces the predetermined nerve response.

6. The apparatus of claim 4, wherein the nerve response is determined from at least one EMG measured at a muscle physiologically coupled to the nerve.

7. The apparatus of claim 4, further comprising means for determining the nerve status has changed when the energy level of the first electrical signal is not substantially equal to the energy level of the fourth electrical signal.

8. An article of manufacture for use in determining nerve status, the article of manufacture comprising computer readable storage media including program logic embedded therein that causes control circuitry to perform the steps of:

(a) applying a first electrical signal to a first conductive element where the first conductive element is located at a position where the distance between the first conductive element and the nerve is relatively constant and the first electrical signal has an energy level that induces a predetermined nerve response;

(b) applying a second electrical signal to a second conductive element where the second electrical signal has an energy level that induces the predetermined nerve response;

(c) applying a third electrical signal to the second conductive element where the third electrical signal has an energy level that induces the predetermined nerve response;

(d) when the energy level of the third electrical signal is not substantially equal to the energy level of the second electrical signal applying a fourth electrical signal to the first conductive element where the fourth electrical signal has an energy level that induces the predetermined nerve response; and (e) determining the nerve status has changed when the energy level of the first electrical signal is not substantially equal to the energy level of the fourth electrical signal.

9. The article of manufacture of claim 8, wherein the first electrical signal has a current level that induces the predetermined nerve response.

10. The article of manufacture of claim 8, wherein the nerve response is determined from at least one EMG measured at a muscle physiologically coupled to the nerve.

11. An article of manufacture for use in determining relative movement between a nerve and a second conductive element, the article of manufacture comprising computer readable storage media including program logic embedded therein that causes control circuitry to perform the steps of:

(a) applying a first electrical signal to a first conductive element where the first conductive element is located at a position where the distance between the first conductive element and the nerve is relatively constant and the first electrical signal has an energy level that induces a predetermined nerve response;

(b) applying a second electrical signal to the second conductive element where the second electrical signal has an energy level that induces the predetermined nerve response;

(c) applying a third electrical signal to the second conductive element where the third electrical signal has an energy level that induces the predetermined nerve response;

(d) when the energy level of the third electrical signal is not substantially equal to the energy level of the second electrical signal applying a fourth electrical signal to the first conductive element where the fourth electrical signal has an energy level that induces the predetermined nerve response; and (e) determining that relative movement between the nerve and the second conductive element has occurred when the energy level of the first electrical signal is substantially equal to the energy level of the fourth electrical signal.

12. The article of manufacture of claim 11, wherein the first electrical signal has a current level that induces the predetermined nerve response.

13. The article of manufacture of claim 11, wherein the nerve response is determined from at least one EMG measured at a muscle physiologically coupled to the nerve.

14. The article of manufacture of claim 11, further comprising the step of determining the nerve status has changed when the energy level of the first electrical signal is not substantially equal to the energy level of the fourth electrical signal.

15. A method of determining nerve status comprising the steps of:

(a) applying a first electrical signal to a first conductive element where the first conductive element is located at a position where the distance between the first conductive element and the nerve is relatively constant and the first electrical signal has an energy level that induces a predetermined nerve response;

(b) applying a second electrical signal to a second conductive element where the second electrical signal has an energy level that induces the predetermined nerve response;

(c) applying a third electrical signal to the second conductive element where the third electrical signal has an energy level that induces the predetermined nerve response;

(d) when the energy level of the third electrical signal is not substantially equal to the current level of the second electrical signal applying a fourth electrical signal the first conductive element where the fourth electrical signal has an energy level that induces the predetermined nerve response; and (e) determining the nerve status has changed when the energy level of the first electrical signal is not substantially equal to the energy level of the fourth electrical signal.

16. The method of claim 15, wherein step a) includes:

(i) placing a first conductive element at a position where the distance between the first conductive element and the nerve is relatively constant; and (ii) applying a first electrical signal to the first conductive element where the first electrical signal has an energy level that induces a predetermined nerve response.

17. The method of claim 15, wherein the first electrical signal has a current level that induces the predetermined nerve response.

18. The method of claim 15, wherein the nerve response is determined from at least one EMG measured at a muscle physiologically coupled to the nerve.

19. A method of determining relative movement between a nerve and a second conductive element comprising the steps of:
  (a) applying a first electrical signal to a first conductive element where the first conductive element is located at a position where the distance between the first conductive element and the nerve is relatively constant and the first electrical signal has an energy level that induces a predetermined nerve response;
  (b) applying a second electrical signal to the second conductive element where the second electrical signal has an energy level that induces the predetermined nerve response;
  (c) applying a third electrical signal to the second conductive element where the third electrical signal has an energy level that induces the predetermined nerve response;
  (d) when the energy level of the third electrical signal is not substantially equal to the energy level of the second electrical signal applying a fourth electrical signal to the first conductive element where the fourth electrical signal has an energy level that induces the predetermined nerve response; and
  (e) determining that relative movement between the nerve and the second conductive element has occurred when the energy level of the first electrical signal is substantially equal to the energy level of the fourth electrical signal.

20. The method of claim 19, wherein step a) includes:
  (i) placing a first conductive element at a position where the distance between the first conductive element and the nerve is relatively constant; and
  (ii) applying a first electrical signal to the first conductive element where the first electrical signal has an energy level that induces a predetermined nerve response.

21. The method of claim 19, wherein the first electrical signal has a current level that induces the predetermined nerve response.

22. The method of claim 19, wherein the nerve response is determined from at least one EMG measured at a muscle physiologically coupled to the nerve.

23. The method of claim 22, further comprising the step of determining the nerve status has changed when the energy level of the first electrical signal is not substantially equal to the energy level of the fourth electrical signal.

* * * * *